(12) United States Patent
Bade et al.

(10) Patent No.: US 9,272,258 B2
(45) Date of Patent: Mar. 1, 2016

(54) PROCESS FOR PREPARING ALKENYLHALOSILANES AND REACTOR SUITABLE THEREFORE

(71) Applicants: Stefan Bade, Michelbach le Haut (FR); Norbert Schladerbeck, Kelkheim (DE)

(72) Inventors: Stefan Bade, Michelbach le Haut (FR); Norbert Schladerbeck, Kelkheim (DE)

(73) Assignee: EVONIK DEGUSSA GmbH, Essen (DE)

(*) Notice: Subject to any disclaimer, the term of this patent is extended or adjusted under 35 U.S.C. 154(b) by 0 days.

(21) Appl. No.: 14/416,989

(22) PCT Filed: May 28, 2013

(86) PCT No.: PCT/EP2013/060910
§ 371 (c)(1),
(2) Date: Jan. 23, 2015

(87) PCT Pub. No.: WO2014/016014
PCT Pub. Date: Jan. 30, 2014

(65) Prior Publication Data
US 2015/0202590 A1 Jul. 23, 2015

(30) Foreign Application Priority Data
Jul. 24, 2012 (DE) .......................... 10 2012 212 915

(51) Int. Cl.
*C07F 7/12* (2006.01)
*B01J 19/24* (2006.01)

(52) U.S. Cl.
CPC ............. *B01J 19/2415* (2013.01); *C07F 7/122* (2013.01); *B01J 2219/00051* (2013.01); *B01J 2219/00123* (2013.01); *B01J 2219/00162* (2013.01); *B01J 2219/00164* (2013.01); *B01J 2219/00166* (2013.01); *B01J 2219/00245* (2013.01)

(58) Field of Classification Search
USPC ........................................ 556/473, 478, 481
See application file for complete search history.

(56) References Cited

U.S. PATENT DOCUMENTS

| | | | |
|---|---|---|---|
| 2,770,634 A | 11/1956 | Weyenberg | |
| 5,075,480 A | 12/1991 | Hange et al. | |
| 5,808,128 A * | 9/1998 | Fiolitakis | ...................... 556/481 |

FOREIGN PATENT DOCUMENTS

| | | | |
|---|---|---|---|
| DE | 936 445 B | 12/1955 | |
| DE | 197 27 576 A1 | 5/1998 | |
| DE | 199 18 115 A1 | 10/2000 | |
| EP | 1 180 521 A1 | 2/2002 | |
| EP | 1180521 A1 * | 2/2002 | ............... C07F 7/12 |
| WO | WO 2014/016013 A1 | 1/2014 | |

OTHER PUBLICATIONS

International Search Report issued Jul. 25, 2013 in PCT/EP2013/060910 Filed May 28, 2013.
German Search Results issued Oct. 22, 2012 in Patent Application No. DE 10 2012 212 915.4 Filed Jul. 24, 2012.
U.S. Appl. No. 14/416,952, filed Jan. 23, 2015, Bade, et al.

* cited by examiner

*Primary Examiner* — Sudhakar Katakam
*Assistant Examiner* — Pancham Bakshi
(74) *Attorney, Agent, or Firm* — Oblon, McClelland, Maier & Neustadt, L.L.P.

(57) ABSTRACT

A process for preparing alkenylhalosilanes by reacting alkenyl halide in the gas phase in a reactor comprising a reaction tube (1) equipped with an inlet (2) at one end of the tube and with an outlet (3) at the other end of the tube, and having a gas inlet device (4) having a plurality of gas feed points (5) that are spaced apart in the direction of the longitudinal axis of the reaction tube (1) and open into the reaction tube (1). The process permits the preparation of alkenylhalosilanes in high yield and with high selectivity. The formation of soot is distinctly lower compared to conventional reactors.

19 Claims, 1 Drawing Sheet

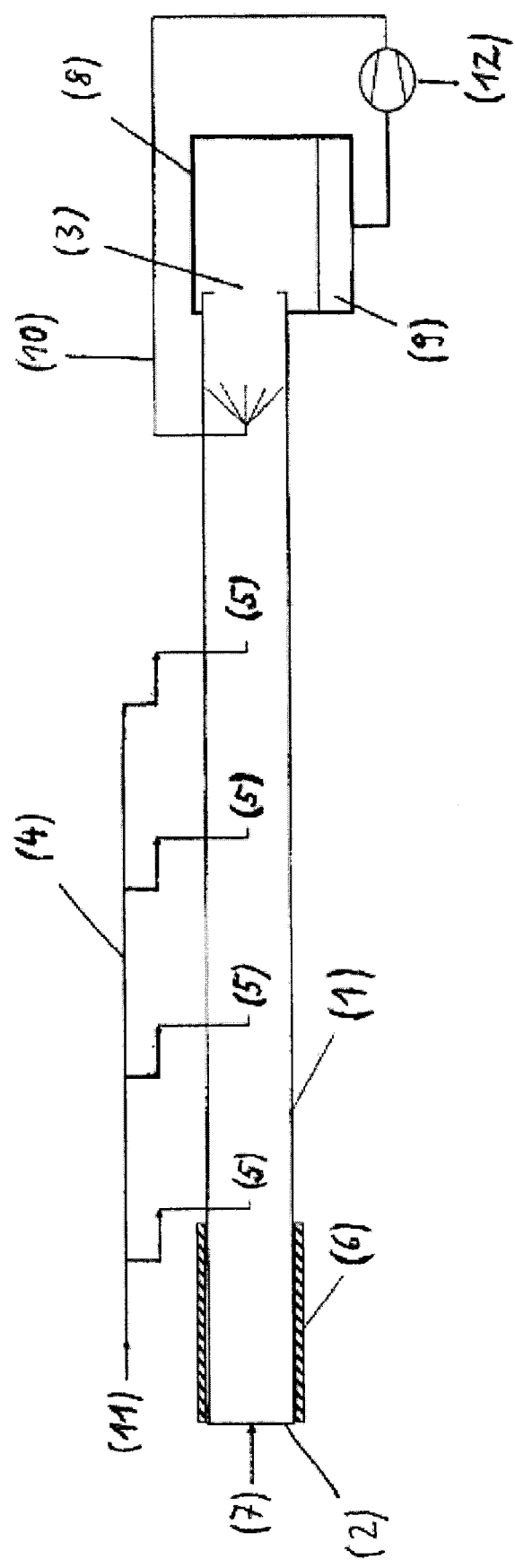

PROCESS FOR PREPARING ALKENYLHALOSILANES AND REACTOR SUITABLE THEREFORE

The present invention relates to a process for preparing alkenylhalosilanes, especially vinyltrichlorosilane, from vinyl chloride and trichlorosilane, and to a reactor particularly suitable therefor.

The industrial scale preparation of alkenylhalosilanes is common knowledge. As a representative example of the preparation of alkenylhalosilanes, the industrial scale preparation of vinyltrichlorosilane (III) is described here in detail. This is effected from the raw materials vinyl chloride (I) and trichlorosilane (II). In a free-radical high-temperature reaction, silane (II) is combined with vinyl chloride (I), with elimination of hydrogen chloride (IV), according to the following reaction scheme (1):

$$C_2H_3Cl(I)+SiHCl_3(II) \rightarrow C_2H_3SiCl_3(III)+HCl(IV) \quad (1)$$
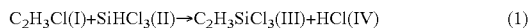

Alkenylhalosilanes, such as vinyltrichlorosilane (III), especially the group of the vinyltrialkoxysilanes prepared from the compound (III) via esterification reactions, are important industrial intermediates and end products in organosilane chemistry. They find use, for example, as crosslinkers in plastics such as PVC, PP and PE.

As well as the main reaction shown above, several unwanted side reactions proceed in the course of conversion. Examples of these include:

A) formation of silicon tetrachloride (V) according to scheme (2) below:

$$SiHCl_3(II)+HCl(IV) \rightarrow SiCl_4(V)+H_2(VI) \quad (2)$$
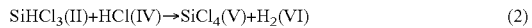

B) formation of bis(trichlorosilyl)ethane (VII) according to scheme (3) below:

$$SiHCl_3(II)+C_2H_3SiCl_3(III)Cl_3SiC_2H_4SiCl_3(VII) \quad (3)$$

C) formation of soot (VIII) according to the following scheme (4):

$$C_2H_3Cl(I) \rightarrow 2C(VIII)+HCl(IV)+H_2(VI) \quad (4)$$
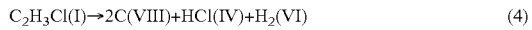

The free-radical exothermic substitution reaction between vinyl chloride and trichlorosilane proceeds typically in a high-temperature reactor within the temperature range between 400 and 700° C. and a pressure between 1 and 2 bar abs. The standard processes are characterized in that either a tubular reactor or a reactor having a rotating displacement body is used. Examples thereof can be found in EP 0 438 666 A2, DE 199 18 114 A1 and DE 199 18 115 A1.

The existing processes have several disadvantages. These are the by-products that form as a result of backmixing, wall reactions that lead, for example, to the formation of soot (reaction scheme 4), and the difficulty of temperature control.

In addition, the conversion of the vinyl chloride can be set only in the range of 80% at maximum, in which case the selectivity based on vinyltrichlorosilane is about 86% at maximum. At conversions of >80%, the selectivity falls considerably because of the side reactions that proceed.

As a result of soot formation in the use of conventional reactors, they have to be shut down and cleaned at regular intervals.

EP 0 438 666 A2 describes an annular gap reactor having a gap measurement of 20 mm. The annular gap is formed by means of a rotating displacement body within the reactor shell. Documents DE 199 18 114 A1 and DE 199 18 115 A1 likewise describe an annular gap reactor for the production of vinyltrichlorosilane, in which the stream, after flowing through the annular gap, runs through an adiabatic reaction zone and then the reaction gases are quenched.

A typical process regime known from DE 199 18 115 A1 results in a vinyl chloride conversion of 85% and a vinyltrichlorosilane selectivity, based on vinyl chloride converted, of 88%. Feeding in 100 kg/h of vinyl chloride and 700 kg/h of trichlorosilane results in the following mass flow rates in the reaction mixture at the reactor outlet:

vinyl chloride=14.9 kg/h trichlorosilane=495.2 kg/h
vinyltrichlorosilane=193.3 kg/h hydrogen chloride=43.6 kg/h
silicon tetrachloride=38.1 kg/h high boilers/further secondary components=15.1 kg/h The production output of the reactor described is 139 t of vinyltrichlorosilane per month or, in specific terms, 900 kg/(m³*h) as the space-time yield.

A typical process regime known from DE 199 18 114 A1 results in a vinyl chloride conversion of 86% and a vinyltrichlorosilane selectivity, based on VC converted, of 89%. Feeding in 70 kg/h of vinyl chloride and 420 kg/h of trichlorosilane results in the following mass flow rates in the reaction mixture at the reactor outlet:

vinyl chloride=9.8 kg/h trichlorosilane=274.8 kg/h
vinyltrichlorosilane=138.5 kg/h hydrogen chloride=32.2 kg/h
silicon tetrachloride=20.8 kg/h high boilers/further secondary components=15.5 kg/h The production output of the annular gap reactor described is 100 t of vinyltrichlorosilane per month or, in specific terms, 648 kg/(m³*h) as the space-time yield.

These two comparative examples describe maximum vinyl chloride conversions of 86%, maximum vinyltrichlorosilane selectivities of 89% and a maximum vinyltrichlorosilane space-time yield of 900 kg/(m³*h).

It has now been found that, surprisingly, use of a novel reactor of the "staged reactor" type allows the yield and selectivity based on the alkenylhalosilane target product, especially of vinyltrichlorosilane (III), to be distinctly increased compared to the existing processes. Furthermore, the process regime is gentle, such that the tendency for side reactions to proceed can be distinctly reduced, and the formation of by-products, such as soot, can be drastically reduced.

The problem addressed by the present invention is that of providing a process and a reactor suitable therefor for preparation of alkenylhalosilanes having increased yield and selectivity compared to known processes and reactors, and having a reduced tendency to side reactions.

The present invention relates to a process for preparing alkenylhalosilanes by reacting alkenyl halide selected from the group of vinyl halide, vinylidene halide and allyl halide with halosilane selected from the group of mono-, di- and trihalosilane in the gas phase in a reactor comprising a reaction tube (1) equipped with an inlet (2) at one end of the tube and with an outlet (3) at the other end of the tube, and having a gas inlet device (4) having a plurality of gas feed points (5) which are spaced apart in the direction of the longitudinal axis of the reaction tube (1) and open into the reaction tube (1), wherein mono-, di- or trihalosilane is passed through the inlet (2) into the reaction tube (1) and flows through the reaction tube (1) in the direction of outlet (3), and wherein vinyl halide, vinylidene halide or allyl halide flows through the gas feed points (5) in sections into the gas stream in the interior of the reaction tube (1).

In the context of this description, halogen is understood to mean fluorine, chlorine, bromine or iodine, preferably chlorine and bromine, especially chlorine.

The vinyl halides used in accordance with the invention are vinyl fluoride, vinyl chloride, vinyl bromide and vinyl iodide, or mixtures of two or more thereof. Preference is given to using vinyl chloride and/or vinyl bromide, most preferably vinyl chloride.

The vinylidene halides used in accordance with the invention are vinylidene fluoride, vinylidene chloride, vinylidene bromide and vinylidene iodide, or mixtures of two or more thereof. Preference is given to using vinylidene chloride and/or vinylidene bromide, most preferably vinylidene chloride.

The allyl halides used in accordance with the invention are allyl fluoride, allyl chloride, allyl bromide and allyl iodide, or mixtures of two or more thereof. Preference is given to using allyl chloride and/or allyl bromide, most preferably allyl chloride.

The monohalosilanes used in accordance with the invention are monofluorosilane, monochlorosilane, monobromosilane and monoiodosilane, or mixtures of two or more thereof. Preference is given to using monochlorosilane and/or monobromosilane, most preferably monochlorosilane.

The dihalosilanes used in accordance with the invention are compounds of the formula $(Hal1)(Hal2)SiH_2$ where Hal1 and Hal2 are each independently fluorine, chlorine, bromine or iodine. Examples of dihalosilanes are difluorosilane, dichlorosilane, dibromosilane, diiodosilane or mixed types, such as chlorobromosilane, fluorochlorosilane or chloroiodosilane. Mixtures of two or more thereof may also be involved. Preference is given to using dihalosilanes in which Hal1 and Hal2 are the same. Very particular preference is given to using dichlorosilane and/or dibromosilane, and especially dichlorosilane.

The trihalosilanes used in accordance with the invention are compounds of the formula $(Hal1)(Hal2)(Hal3)SiH$ where Hal1, Hal2 and Hal3 are each independently fluorine, chlorine, bromine or iodine. Examples of trihalosilanes are trifluorosilane, trichlorosilane, tribromosilane, triiodosilane or mixed types, such as fluorochlorobromosilane, dichlorobromosilane or chlorodibromosilane. Mixtures of two or more thereof may also be involved. Preference is given to using trihalosilanes in which Hal1, Hal2 and Hal3 are the same. Very particular preference is given to using trichlorosilane and/or tribromosilane, and especially trichlorosilane.

Very particular preference is given to reacting trichlorosilane and vinyl chloride or trichlorosilane and allyl chloride with one another.

In the inventive reactor, the alkenyl halide is fed into the flowing mono-, di- or trihalosilane gas stream via a plurality of gas feed points (5). The gas feed points (5) are arranged spaced apart in the direction of the longitudinal axis of the reaction tube (1) and permit the introduction of gas in sections of the reaction tube (1). The gas feed points (5) preferably open into the middle of the reaction tube (1), such that the gas introduced is introduced in sections at the site of the longitudinal axis of the reaction tube (1). Also possible, however, are variants in which one or more gas feed points (5) do not open into the middle at the site of the longitudinal axis of the reaction tube (1). The reactor has low backmixing and the reactions are kept away from the reactor wall, which leads to reduced formation of by-products.

In addition, the reaction regime (=division of the alkenyl halide stream between several feed points in the reactor) produces an optimal temperature profile in the reactor, as a result of which the selectivity and space-time yield based on the alkenylhalosilane target product can be increased in a particularly advantageous manner.

The avoidance of rotating internals, as described in EP 0 438 666 A2, DE 199 18 114 A1 and DE 199 18 115 A1, makes the construction of the reactor much simpler and less demanding in terms of maintenance.

The mono-, di- or trihalosilane can be fed into the reaction tube (1) entirely at the inlet (2) in the process according to the invention. Alternatively, a portion of the mono-, di- or trihalosilane can be fed into the reaction tube (1) at the inlet (2) and the remaining portion is fed into the middle of the reaction tube (1) via one or more gas inlet devices (4).

Preference is given to a process wherein only mono-, di- or trihalosilane is fed in at the inlet (2), while alkenyl halide is fed into the gas mixture flowing in the interior of the reaction tube (1) at several points distributed over the length of the reaction tube (1). The alkenyl halide is especially introduced into the main flow direction.

The gas inlet device (4) provides gas feed points (5) for the alkenyl halide into the reaction tube (1). The number of gas feed points (5) may vary over a wide range. Typically, two to ten gas feed points (5), preferably three to six gas feed points (5), are provided.

The distance between two gas feed points (5) may likewise vary within wide ranges. Typically, this distance is between 100 mm and 2000 mm. The gas feed points (5) are preferably arranged equidistantly, but any other arrangement may also be chosen.

The alkenyl halide is generally fed into the reactor after the mono-, di- or trihalosilane has been fed in. Typically, the distance between the first gas feed point (5) and the inlet (2) is between 20 mm and 1000 mm.

By varying the flow rate of the alkenyl halide at the gas feed points (5), the course of the reaction can be controlled. Preferably, therefore, means by which the flow rate of the alkenyl halide to the gas feed points (5) can be varied are provided in the gas inlet device (4).

Preferably, the flow rate of the alkenyl halide is divided equally between the different gas feed points (5); alternatively, the flow rate of the alkenyl halide can be varied as desired between the different gas feed points (5). Preferably, a flow rate of alkenyl halide/(n·5) is chosen as the minimum amount per gas feed point (5), and a flow rate of alkenyl halide/(n·½) is chosen as the maximum amount per gas feed point (5). In this context, n is the total number of gas feed points (5) in the reactor; n is suitably greater than or equal to 2, preferably 3 to 15, more preferably 4 to 13, even more preferably 5 to 12, and especially also 6, 7, 8, 9, 10 and 11.

The reaction can likewise be controlled via the use ratio of mono-, di- or trihalosilane to alkenyl halide. Typically, the use ratio of mono-, di- or trihalosilane to alkenyl halide is between 1.0 and 10 mol:mol, preferably between 2.0 and 4.0 mol:mol.

At the end of the reaction tube (1), the reaction of mono-, di- or trihalosilane with alkenyl halide has substantially concluded. The product-containing reaction mixture can be discharged from the reaction tube (1) via the outlet (3) and sent to further operations, for example a separation of the alkenylhalosilane product from the reaction mixture.

Preferably, the hot reaction mixture is quenched at the product end of the reaction tube (1). This can preferably be effected with liquid crude product, which is preferably injected into the hot reaction mixture at the product end of the reaction tube (1).

In the process according to the invention, the reaction temperature can be chosen within wide ranges. Preferably, the temperature in the interior of the reaction tube (1) (=the reaction temperature) is between 400 and 700° C., more preferably between 500 and 650° C.

In the process according to the invention, the reaction pressure can likewise be chosen within wide ranges. Preferably, the pressure in the interior of the reaction tube (1) (=reaction pressure) is between 1.0 and 2.0 bar abs, more preferably between 1.0 and 1.5 bar abs.

The course of the reaction can be controlled by the amount of the reactants added. Preferably, the component flow rates of alkenyl halide at the feed points are set in a controlled manner. The control can be effected by means of closed-loop temperature control circuits at the gas feed points (5).

The residence time of the reaction mixture in the reactor can likewise be varied over wide ranges. Typically, the residence time of the reaction mixture in the reactor from the first gas feed point (5) to the outlet (3) varies within the range between 0.5 and 10 sec, preferably between 1.5 and 4 sec.

The present invention also relates to a tubular reactor suitable for performance of gas phase reactions and especially for performance of the above-described process for preparing alkenylhalosilane.

The inventive reactor is characterized by the presence of at least the following elements:
A) reaction tube (1) having
B) an inlet (2) at one side of the tube,
C) an outlet (3) at the other side of the tube, and
D) having a gas inlet device (4) having a plurality of gas feed points (5) which are spaced apart in the direction of the longitudinal axis of the reaction tube (1) and open into the reaction tube (1).

The injection of the reactants in sections through several gas feed points (5) that open into the reaction tube (1) brings about a reaction regime in sections, such that the inventive reactor can also be referred to as a staged reactor.

The materials from which both the reaction tube (1) and the gas inlet device (4) are produced are stable at high temperatures. These materials include, for example, ferrous alloys, for example scale-resistant steels containing, as well as iron, chromium, nickel and/or titanium and/or molybdenum as alloy constituent.

The reactor for preparation of alkenylhalosilanes by reaction of alkenyl halide with mono-, di- or trihalosilanes may be arranged horizontally, vertically, or else obliquely. The way in which the reactor has been mounted has no influence on the alkenylhalosilane yields of the reaction unit. It has been found, however, that the service life of the reactors arranged vertically is much longer than that of reactors which are operated in a horizontal position.

The reactor, i.e. the outer reaction tube (1), can be heated in a wide variety of different ways. The most frequently used method involves the direct electrical heating of the outer surface of the reaction tube (1). Another form of heating involves heating the outer tube by means of an intervening medium, for example liquid lead. It is also possible to heat the outer tube by means of gas flames or by means of infrared radiation. The way in which the reactor is heated has only an insignificant effect on the conversions achievable per unit of cross-sectional area of the reactor.

Preference is given to a reactor in which, in a preheating zone (6) connected to the inlet (2), the reactant (7) is heated to the required reaction temperature in the interior of the reaction tube (1).

Preference is given to a reactor in which the outlet (3) opens into a reservoir vessel (8) for the cooled product (9).

In this reactor variant, a line (10) through which a portion of the product (9) is recycled close to the outlet (3) and is injected into the reaction mixture present at that point is preferably provided, and this brings about shock cooling of the reaction mixture and formation of the cooled product (9).

FIG. 1 describes the process according to the invention and the reactor according to the invention. This shows the reaction tube (1) equipped on the left-hand side with an inlet (2) for a reactant (7), for example for trichlorosilane. In a preheating zone (6) connected to the inlet (2), the reactant (7) is heated to the required reaction temperature. Several gas feed points (5) which are fed by a gas inlet device (4) open into the reaction tube (1). The opening of each of these gas feed points (5) is in the middle of the tube cross section. Through the gas feed points (5), a further reactant (11), for example vinyl chloride, is injected in sections into the reaction mixture within the interior of the reaction tube (1). The reaction tube (1) ends on the right-hand side with an outlet (3) for the reaction mixture. This outlet (3) opens into a reservoir vessel (8) for the cooled product (9). A portion of the product (9) is recycled via line (10), under the action of the pump (12), close to the outlet (3) and is injected into the reaction mixture present at that point. This results in shock cooling of the reaction mixture and formation of the cooled product (9). This is then passed via outlet (3) into the reservoir vessel (8).

The example below describes the invention in specific detail, without any intention of limitation thereby.

Vinyl chloride was reacted with trichlorosilane in a staged reactor (diameter 200 mm, length 6000 mm) to give vinyltrichlorosilane. The trichlorosilane reactant was preheated here to 400° C. in a preheating zone. At the top of the reactor was the feed for trichlorosilane. Vinyl chloride was injected, likewise in gaseous and preheated form, via several feed points each distributed in the middle of the axis of the tubular reactor. On exit of the vinyl chloride at the feed points, the vinyl chloride was encased by trichlorosilane, and the reaction to give vinyltrichlorosilane then took place in short reaction zones, with avoidance of the disadvantageous wall reaction. The trichlorosilane fed in was fed in excess and was therefore never consumed completely at the vinyl chloride feed points. The result was a pure gas phase reaction between trichlorosilane and vinyl chloride at the vinyl chloride feed points. The yield-reducing wall reactions which lead to the formation of soot, for example, were prevented.

The reaction proceeded continuously in the staged reactor described, with feeding of vinyl chloride in sections into the hot trichlorosilane stream.

The reactor can in principle be regarded as a low-backmixing tubular reactor. By means of the distribution of the vinyl chloride stream between several feed points, it was possible to optimize the temperature regime in the reactor. At the end of the reactor, there was a quench of the hot reaction gases with liquid crude product, which very substantially suppressed further reaction to give silicon tetrachloride (V).

In the example, 650 kg/h of trichlorosilane were fed in at 400° C. at the reactor inlet. In the first part of the reactor, the trichlorosilane stream was heated further to about 550° C. The first portion of vinyl chloride (25 kg/h) was fed into the hot trichlorosilane stream at z=800 mm (=distance measured from the left-hand edge of the reactor). There followed three further vinyl chloride feeds at a distance of 1000 mm, at each of which 25 kg/h of vinyl chloride were also fed in. 1000 mm beyond the fourth and last feed point, the hot reaction gas was quenched to about 40° C. with liquid crude product. The vinyl chloride conversion was 86%; the selectivity was 95%.

The reactor used had a diameter of 200 mm and a length of 6000 mm. The following mass flow rates of the reaction mixture at the reactor outlet were found:
vinyl chloride=14.0 kg/h trichlorosilane=447.9 kg/h
vinyltrichlorosilane=211.1 kg/h hydrogen chloride=47.6 kg/h
silicon tetrachloride=17.4 kg/h high boilers/further secondary components=11.8 kg/h Thus, this reactor had a monthly production output of 152 t of vinyltrichlorosilane and a space-time yield of 1120 kg/(m$^3$*h). A higher space-time yield was achieved than in the above-described comparative examples with prior art reactors, and the vinyltrichlorosilane selectivity of the staged reactor used, at 95%, was likewise higher than in the comparative examples. The higher vinyltrichlorosilane selectivity was achieved by virtue of a lower incidence of silicon tetrachloride by-product and of high boilers or further secondary components.

Advantages of the process according to the invention and of the reactor of the "staged reactor" type according to the invention are found to be the enhanced selectivity and the enhanced space-time yield based on the vinyltrichlorosilane target product, because wall reactions are selectively prevented through the encasement with a trichlorosilane stream. Moreover, the reactor can be described as having low backmixing, as a result of which a lower level of by-products, for example silicon tetrachloride, soot and 1,2-bis(trichlorosilyl) ethane, is formed in the reaction system in question. In addition, the feeding of vinyl chloride in sections establishes an optimal temperature profile, as a result of which particularly the side reaction (2) to give silicon tetrachloride (V) is minimized.

By virtue of the wall reaction being very substantially prevented through the flanking with trichlorosilane, the formation of soot is minimized and the intervals for the cleaning operations of the reactor are extended. The staged reactor used in accordance with the invention can be operated with a distinctly increased vinyl chloride conversion and vinyl chloride throughput, because it works with low backmixing. This increases the space-time yield of vinyltrichlorosilane compared to the reactants used conventionally. Through the optimization of the number of vinyl chloride feed points and through the optimization of the amounts of vinyl chloride fed in, the temperature profile can be optimized so as to maximize the selectivity based on vinyltrichlorosilane. Ideally, the component vinyl chloride flow rates at the feed points are controlled via closed-loop temperature control circuits. In addition, the feed points for vinyl chloride are preferably provided with a 90° curve, such that the vinyl chloride is introduced with the flow direction.

The invention claimed is:

1. A process for preparing alkenylhalosilanes, the method comprising
reacting alkenyl halide selected from the group of vinyl halide, vinylidene halide and allyl halide with halosilane selected from the group of monohalosilane, a dihalosilane, and trihalosilane in the gas phase in a reactor comprising a reaction tube comprising an inlet at one end of the tube, an outlet at the other end of the tube, and a gas inlet device comprising a plurality of gas feed points which are spaced apart in the direction of the longitudinal axis of the reaction tube and open into the reaction tube, wherein the halosilane is passed through the inlet into the reaction tube and flows through the reaction tube in the direction of outlet, and alkenyl halide is fed through the plurality of gas feed points into the gas stream in the interior of the reaction tube.

2. The process according to claim 1, wherein the alkenyl halide is vinyl chloride, vinyl bromide, vinylidene chloride, vinylidene bromide, allyl chloride or allyl bromide, and the halosilane is dichlorosilane, trichlorosilane, dibromosilane, or tribromosilane.

3. The process according to claim 1, wherein the alkenyl halide is vinyl chloride or allyl chloride, and the halosilane is trichlorosilane.

4. The process according to claim 1, wherein only the halosilane is fed in at the inlet and the alkenyl halide is fed into the gas mixture flowing in the interior of the reaction tube through the plurality of gas feed points.

5. The process according to claim 1, wherein the alkenyl halide is fed through the plurality of feed points with a gas inlet device into the middle of the tubular reactor via two to ten gas feed points, and the distance between a first gas feed point and the inlet is from 20 mm to 1000 mm.

6. The process according to claim 5, wherein a distance between two gas feed points is from 100 mm to 2000 mm.

7. The process according to claim 1, wherein the alkenyl halide is fed and controlled through the plurality of gas feed points with a gas inlet device.

8. The process according to claim 7, wherein the flow rate of the alkenyl halide is divided equally between the plurality of gas feed points, or the flow rate of the alkenyl halide is varied between the plurality of gas feed points, such that the flow rate of the alkenyl halide at minimum for a single gas feed point is a flow rate of alkenyl halide/(n·5), and at maximum a flow rate of alkenyl halide/(n·½), wherein n is the total number of gas feed points in the reactor and n≥2.

9. The process according to claim 1, wherein the halosilane to alkenyl halide are reacted in a ratio of 1.0 to 10 mol:mol.

10. The process according to claim 1, wherein a hot reaction mixture is obtained at the outlet of the reaction and the hot reaction mixture is quenched with a liquid crude product at the end of the reaction tube.

11. The process according to claim 1, wherein the interior of the reaction tube has a temperature of 400 to 700° C.

12. The process according to claim 1, wherein the interior of the reaction tube has a pressure of 1.0 to 2.0 bar abs.

13. The process according to claim 1, wherein the alkenyl halide is fed to the plurality of gas feed points with closed-loop temperature control circuits.

14. The process according to claim 1, wherein the alkenyl halide and the halosilane have a residence time in the reactor from a first gas feed point to the outlet of from 0.5 to 10 sec.

15. The process according to claim 5, wherein a distance between two gas feed points is between is from 100 mm to 2000 mm, and the gas feed points are arranged equidistantly.

16. The process according to claim 1, wherein the halosilane to alkenyl halide are reacted in a ratio of 2.0 to 4.0 mol:mol.

17. The process according to claim 1, wherein the interior of the reaction tube has a temperature of 500 to 650° C.

18. The process according to claim 1, wherein the interior of the reaction tube has a pressure of 1.0 to 1.5 bar abs.

19. The process according to claim 1, wherein the alkenyl halide and the halosilane have a residence time in the reactor from a first gas feed point to the outlet of from 1.5 to 4 sec.

* * * * *